(12) United States Patent
Miller

(10) Patent No.: US 7,951,199 B2
(45) Date of Patent: May 31, 2011

(54) LATERAL EXPANDABLE INTERBODY FUSION CAGE

(76) Inventor: Jimmy D. Miller, Southaven, MS (US)

( * ) Notice: Subject to any disclaimer, the term of this patent is extended or adjusted under 35 U.S.C. 154(b) by 814 days.

(21) Appl. No.: 11/152,251

(22) Filed: Jun. 15, 2005

(65) Prior Publication Data

US 2006/0287725 A1 Dec. 21, 2006

(51) Int. Cl.
*A61F 2/44* (2006.01)
(52) U.S. Cl. .................................... 623/17.11
(58) Field of Classification Search ............... 606/61, 606/246–249; 623/16.11, 17.11–17.16
See application file for complete search history.

(56) References Cited

U.S. PATENT DOCUMENTS

| | | | | |
|---|---|---|---|---|
| 3,622,029 A * | 11/1971 | Ware | ............................. | 220/3.7 |
| 5,574,255 A * | 11/1996 | Simmons | ........................ | 174/53 |
| 5,595,431 A * | 1/1997 | Mlakar | ........................ | 312/409 |
| 6,176,882 B1 * | 1/2001 | Biedermann et al. | ...... | 623/17.15 |
| 6,436,140 B1 | 8/2002 | Liu et al. | | |
| 6,743,255 B2 | 6/2004 | Ferree | | |
| 6,833,006 B2 * | 12/2004 | Foley et al. | ................ | 623/17.11 |
| 2002/0151976 A1 * | 10/2002 | Foley et al. | ................ | 623/17.11 |
| 2003/0040799 A1 * | 2/2003 | Boyd et al. | ................. | 623/17.11 |
| 2003/0149484 A1 * | 8/2003 | Michelson | ................. | 623/17.16 |
| 2003/0167091 A1 * | 9/2003 | Scharf | ........................ | 623/17.11 |
| 2004/0117017 A1 * | 6/2004 | Pasquet et al. | ............ | 623/17.11 |
| 2004/0127990 A1 * | 7/2004 | Bartish et al. | ............. | 623/17.11 |
| 2004/0172134 A1 * | 9/2004 | Berry | ........................ | 623/17.11 |
| 2005/0256576 A1 * | 11/2005 | Moskowitz et al. | ....... | 623/17.12 |
| 2006/0074488 A1 * | 4/2006 | Abdou | ........................ | 623/17.11 |

\* cited by examiner

*Primary Examiner* — Eduardo C Robert
*Assistant Examiner* — Tara R Carter
(74) *Attorney, Agent, or Firm* — Browdy and Neimark, PLLC

(57) ABSTRACT

A lateral expandable interbody fusion cage expands laterally between two vertebrae to promote fusion between the two vertebrae. The cage includes an outer cage and at least one inner cage, with optional flanges and spikes.

17 Claims, 7 Drawing Sheets

LATERAL EXPANDABLE INTERBODY FUSION CAGE

BACKGROUND OF THE INVENTION

Eighty five percent of the population will experience low back pain at some point. Fortunately, the majority of people recover from their back pain with a combination of benign neglect, rest, exercise, medication, physical therapy, or chiropractic care. A small percentage of the population will suffer chronic low back pain. The cost of treatment of patients with spinal disorders, plus the patients' lost productivity, is estimated to be 25 to 100 billion dollars annually.

Seven cervical neck, twelve thoracic, and five lumbar (low back) vertebrae form the normal human spine. Intervertebral discs reside between adjacent vertebrae with two exceptions: (1) The articulation between the first two cervical vertebrae does not contain a disc; (2) A disc lies between the last lumbar vertebra and the sacrum (a portion of the pelvis).

Motion between vertebrae occurs through the disc and two facet joints. The disc lies in the front or anterior portion of the spine. The facet joints lie laterally on either side of the posterior portion of the spine. The osseous-disc combination of the spine coupled with ligaments, tendons and muscles are essential for spinal function. The spine allows movement (flexion, lateral bending, and rotation), supports the body, and protects the spinal cord and nerves.

The discs change with aging. As a person ages, the water content of the disc falls from approximately 85 percent at birth to about 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally, disc degeneration is painless.

Premature or accelerated disc degeneration is known as degenerative disc disease. A large portion of patients suffering from chronic low back pain are through to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in bulging of the annulus into the spinal cord or nerves; narrowing of the space between the vertebra where the nerves exit; tears of the annulus as abnormal loads are transmitted to the annulus and the annulus is subjected to excessive motion between vertebra; and disc herniation or extrusion of the nucleus through complete annular tears. Disc herniation can also promote arthritis of the facet joints, which in turn may cause back pain.

The problems created by disc degeneration, facet arthritis, and other conditions such as spondylolysis, spondylolisthesis, scoliosis, fracture, tumor, or infection are frequently treated by spinal fusion. Such problems may include pain in the back or legs, nerve injury, risk of future nerve injury, or spinal deformity. The goal of spinal fusion is to successfully "grow" two or more vertebrae together. To achieve this, bone from the patient's body (spine or iliac crest), or from cadavers, is grafted between vertebrae. Alternatively, bone graft substitutes, such as hydroxyl apatite and bone morphogenic protein, may be used.

The bone graft is placed between the vertebrae in the disc space and/or over the posterior elements of the vertebrae (lamina and transverse processes). The surgeon scrapes the vertebrae to create bleeding. Blood flows into the bone gage. The scraped bone, blood clot (hematoma), and the bone graft simulates a fracture. As the patient heals, the "fracture" causes the vertebrae to be fused and heal together.

Spinal instrumentation, including cages, is placed onto or into the spine to immobilize the vertebrae that are going to be fused. Immobilization leads to a higher fusion rate and speeds a patient's recovery by eliminating movement. Existing cages are typically hollow metal or carbon fiber devices placed into the disc space. Often cages have treads, grooves, and teeth of spikes that engage the cerebral endplates. The hollow center is filled with a bone graft. The sides of the cages adjacent to the vertebral end plates contain holes to allow bone growth from one vertebra through the cage to the adjacent vertebra. The bone graft acts as a bridge for bone growth. Cages immobilize the vertebrae and maintain the separation between the vertebrae, a function of the formed disc material. Cages are placed into the disc space after excising a portion of the disc annulus and most of the nucleus. One or two cages may be inserted at each level.

Cages may be placed into the disc space from an anterior or a posterior approach to the spine. Cages may be combined with rods, screws, hooks, or plates. Combining cages with other instrumentation yields a stiffer construct and presumably increases the chance for a successful fusion. If cages are placed from an anterior approach (through the abdomen), the patient must undergo surgery through a second incision over the back (posterior approach) if the surgeon wishes also to insert rods and screws. To avoid two incisions and increased patient morbidity, many surgeons prefer to insert cages from posterior approach. Rods and screws can then be added through the same incision.

Cages currently available for insertion from a posterior approach have some important weaknesses. Since most cages are inserted into the disc space in their final size and shape, the cages must be large enough to extend from vertebra-to-vertebra. Furthermore, the cages must be wide enough to provide stability and provide adequate surface area for the vertebrae to "grow" together. Large cages inserted posteriorly risk nerve injury from retracting the nerves to insert the cage or the edge of the cage during insertion, or extensive bone removal. A portion of the vertebra (lamina, a portion of the facet, and/or the entire facet) is removed to allow cage insertion. Large cages require more bone removal. Some surgeons remove one or both facet joints to safely insert a cage or cages. Revision procedures are more difficult after the facet joints have been removed.

Many cages inserted posteriorly have parallel superior and inferior surfaces. The endplates of the vertebrae form the superior and inferior limits of the disc space. The endplates are not typically parallel in the lumbar spine. Generally, the endplates become closer together as one proceeds toward the posterior portion of the disc space. This alignment creates the normal anterior to posterior curvature of the lumbar spine known as the lordosis. Cages with parallel superior and inferior surfaces either fit tightly posterior and loosely anteriorly, or require removal of additional endplate posteriorly. Alternatively, the vertebrae can be used without lordosis. None of these choices is ideal.

SUMMARY OF THE INVENTION

It is an object of the present invention to overcome the aforesaid deficiencies in the prior art.

It is another object of the present invention to provide a Lateral Expandable Interbody Fusion (LEIF) cage designed for placement between two vertebrae.

It is another object of the present invention to provide a LEIF cage which promotes fusion between two vertebrae.

It is yet another object of the present invention to provide a LEIF cage which expands laterally.

According to the present invention, the cage is constructed to expand laterally, allowing for a larger exposed surface area for fusion. Unexpanded cages of appropriate height are inserted by impacting the cages into the space below the anterior vertebral body lip and the level of the annulus. Once inserted, a cage expander is inserted into the notch used for expansion, moving the inner cage on each side toward the midline. After expansion, the outer cages are open, and may receive graft material.

The cage of the present invention has been illustrated with wings that slide laterally. However, one skilled in the art can appreciate that many other devices for expansion of the cage can be used, such as a ratchet mechanism which holds the cages open once they are expanded, or a turnbuckle mechanism for opening the cage.

Figure 7A:
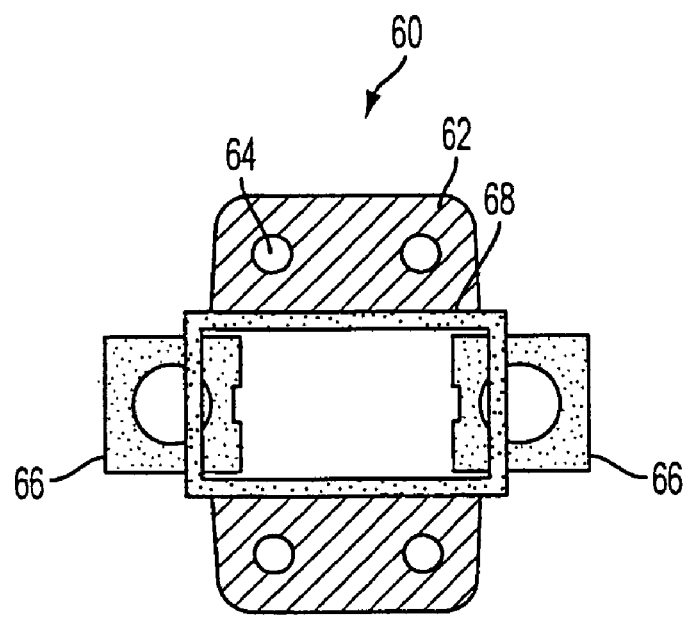

FIG. 7A is an end view of a LEIF cage with an anterior flange to allow screw insertions into the vertebral body above and below.

Figure 7B:
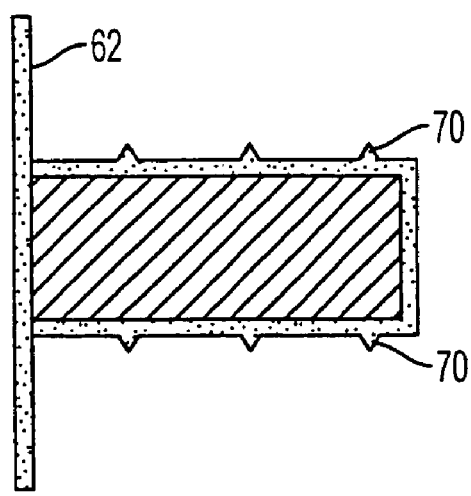

FIG. 7B is a lateral view of the cage.

Figure 8A:
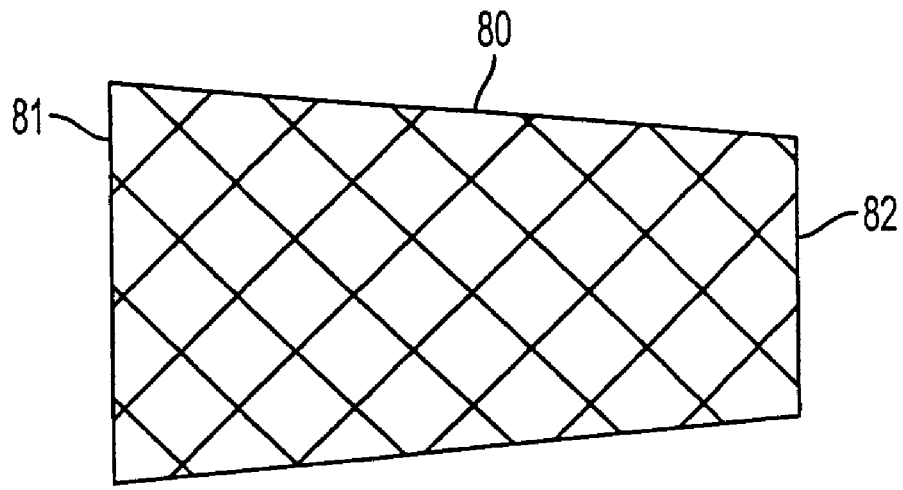

FIG. 8A is a side view of a cage for Anterior Lumbar Interbody Fusion (ALIF).

Figure 8B:
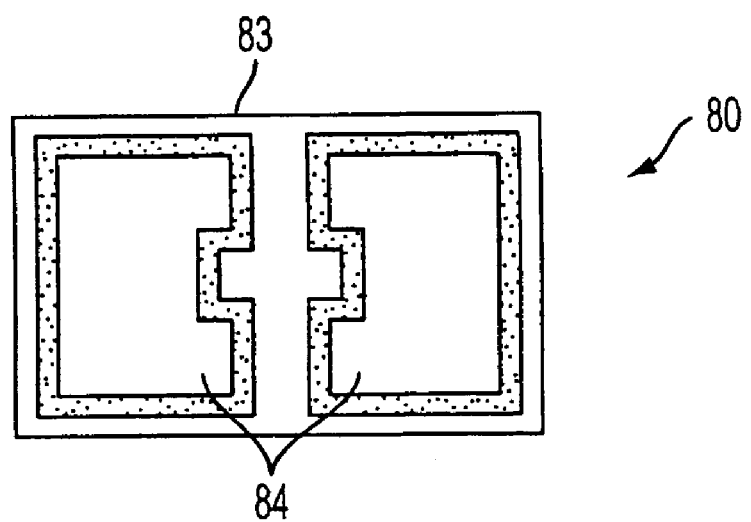

FIG. 8B is an anterior view of a cage for Anterior Lumbar Interbody Fusion (ALIF).

Figure 9A:
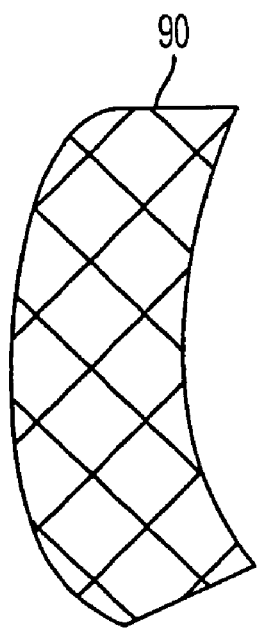

FIG. 9A is a top view of a Transforaminal Lumbar Interbody Fusion cage (TLIF).

Figure 9B:
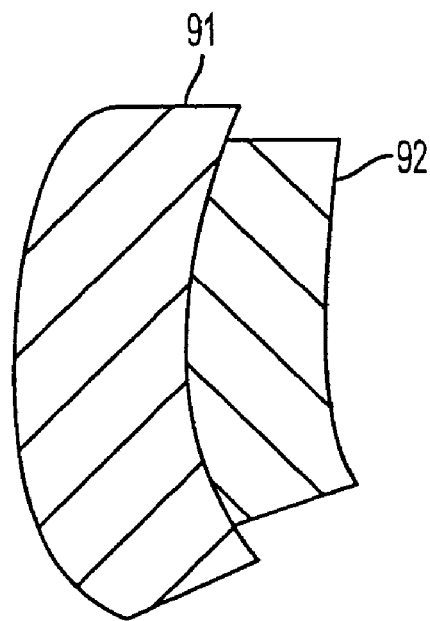

FIG. 9B is a top view of a Transforaminal Lumbar Interbody Fusion cage after expansion.

Figure 10A:
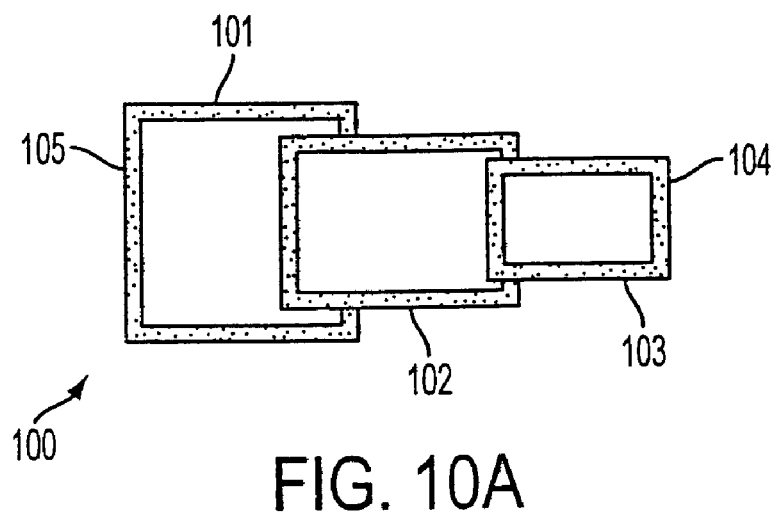

FIG. 10A is another embodiment showing a side view of a TLIF cage.

Figure 10B:
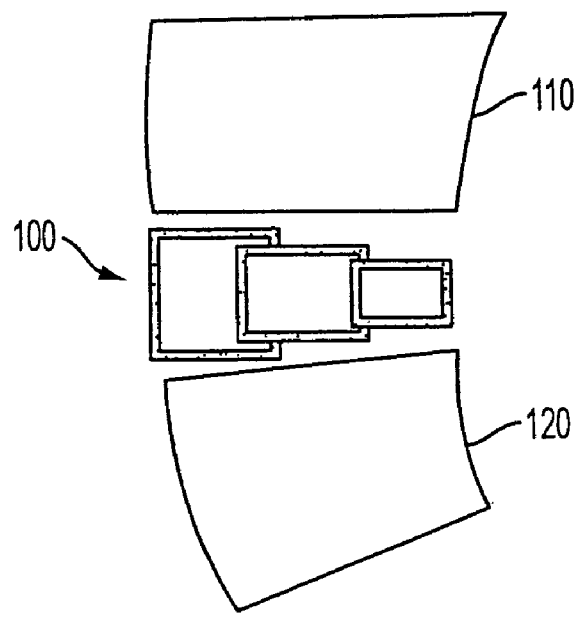

FIG. 10B is a lateral view of a TLIF cage.

DETAILED DESCRIPTION OF THE INVENTION

The laterally expandable interbody fusion cage of the present invention comprises an outer cage 12 and an inner cage 14 that can be inserted sideways into the outer cage 12. The inner cage 14 has a notch 16 for an expander to grip on the front of the inner cage 14. The inner cage 14 can be filled with graft material prior to insertion.

Figure 1A:
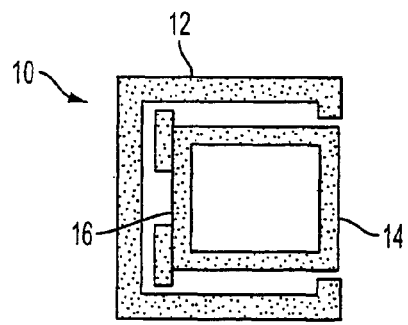
FIG. 1A is an end view of the cage as inserted.
Figure 1B:
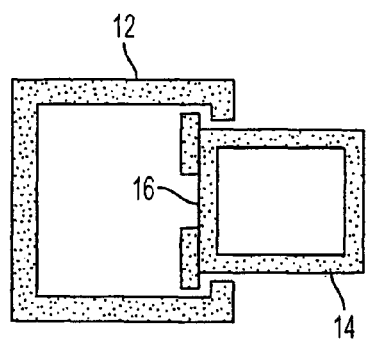
FIG. 1B is an end view of the cage as expanded.

FIG. 1A shows an end view of the cage 10 as inserted, with the inner cage 14 inside of the outer cage 12. FIG. 1B shows an end view of the cage as expanded. With the cage expanded following insertion into the interspace, the outer cage 12 can be filled with graft material.

Figure 2A:
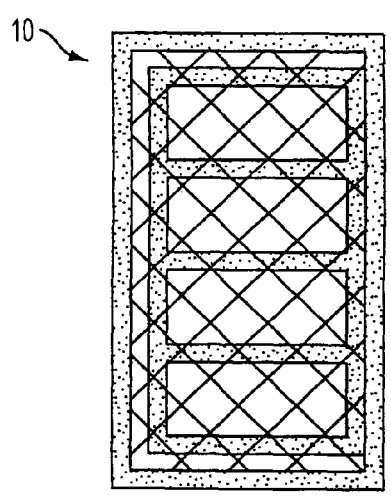
FIG. 2A is a top view of the cage as inserted.
Figure 2B:
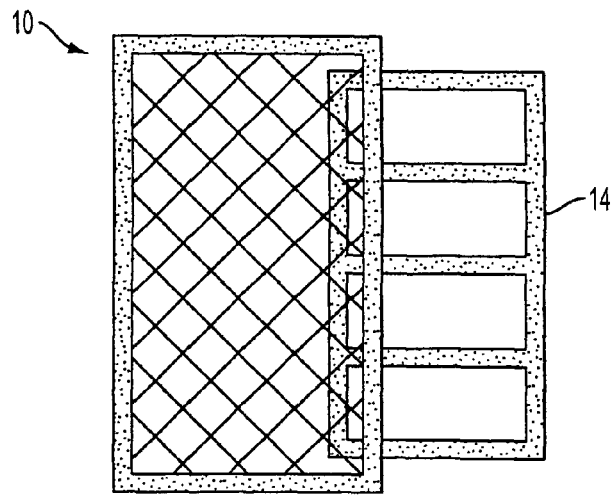
FIG. 2B is a top view of the cage as expanded following insertion.

FIG. 2A shows a top view of the cage 10 as inserted. FIG. 2B shows the right top view of the cage 10 as expanded following insertion. The cage 10 can be expanded by adjusting the position of the inner cage 14 to the desired dimensions.

Figure 3:
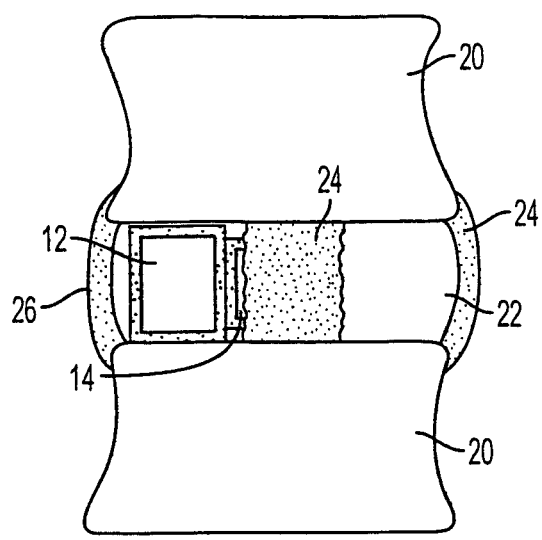
FIG. 3 is a side view of two vertebral bodies with a disc between them and one cage inserted into the left of the disc.

FIG. 3 is a view of two vertebral bodies 20 with a disc between them. Annular windows 22 have been created bilaterally through which cages can be inserted. The end of one cage which has been inserted is visible through the left annular window 22.

Figure 4:
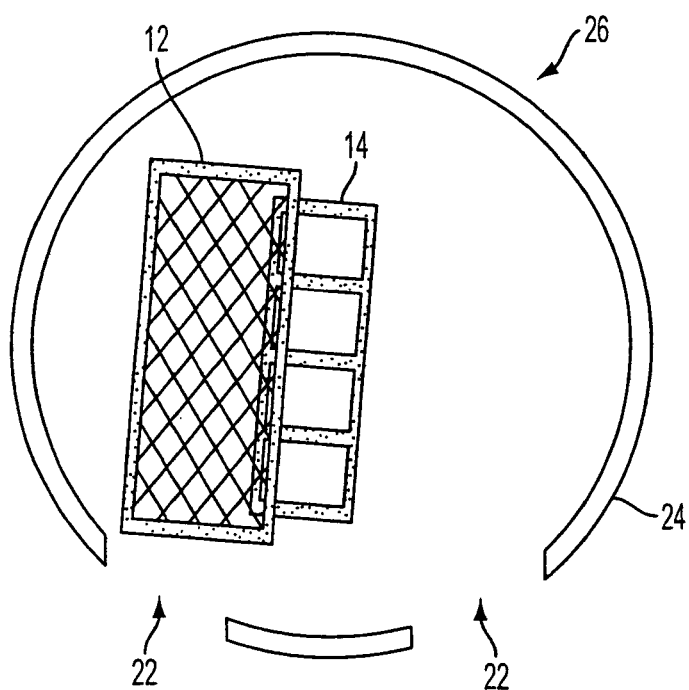
FIG. 4 is a cross sectional view of a disc with annular windows and one cage that has been inserted in the left and expanded laterally.

FIG. 4 is a cross sectional view of a disc annulus 24 with annular windows 22 and one cage that has been inserted on the left and expanded laterally by drawing the inner cage 14 out from the outer cage 12.

Figure 5:
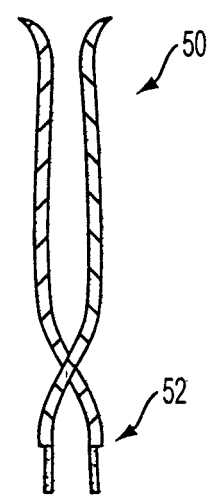
FIG. 5 shows an expander used to expand the inner cage laterally, allowing access to outer cage for filling with graft material.

FIG. 5 is an expander 5 used to expand the inner cage 14 laterally, allowing access to the outer cage 12 for filling.

In inserting the LEIF cage of the present invention, the intervertebral disc is first exposed at surgery. The outer annular fibers 26 are incised with a scalpel to create a window 22 in the interior of the disc. The nucleus pulposus is evacuated via standard surgical technique, with care to remove the disc material toward the midline as well as laterally. If the procedure is being performed by a posterior route, annular windows must be constructed bilaterally. After the nucleus pulposus has been removed sufficiently and the endplates prepared for the cage 10, the cages can be inserted bilaterally.

The open end of the unexpanded LEIF cages are filled with graft material. This graft material fills the inner cage.

The unexpanded cages are then inserted by impacting cages 10 of the appropriate height into the space below the anterior vertebral body lip and the level of the annulus.

Once the cages 10 are inserted, the expander 5 is inserted into the notch used for expansion. The expander 5 is utilized to move the inner cage 14 on each side toward the midline. After expansion of the cages, the outer cages 12 are open, and graft material can be inserted into them.

Figure 6A:
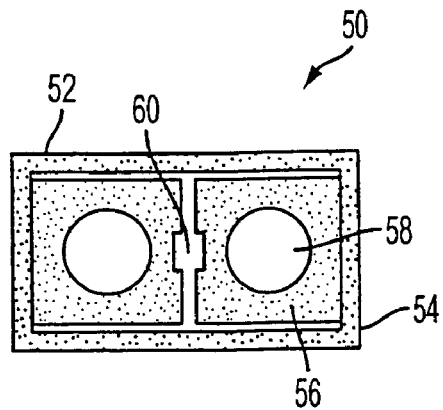
FIG. 6A is an end view of a LEIF cage with two lateral wings closed to allow filling of the wings with graft material.

In another embodiment of the present invention, shown in FIG. 6A, the LEIF cage has two lateral wings in the form of two inner cages 56 which are located side-by-side when the cage 50 is unexpanded and inside the outer cage 52. These inner cages 56 are equipped with a notch 60 to receive an expander for lateral expansion, and 58 a hole into which graft material is inserted.

Figure 6B:
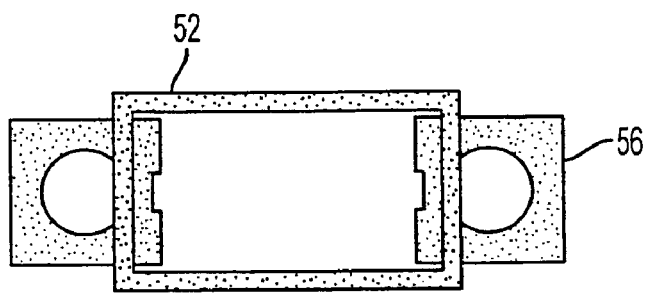
FIG. 6B is an end view of the cage with the two wings opened laterally to allow filling of the outer cage with graft material.

FIG. 6B shows the cage 50 viewed end-on with the two wings or inner cages 56 opened laterally to allow filling of the outer cage 52 with graft material.

Figure 6C:
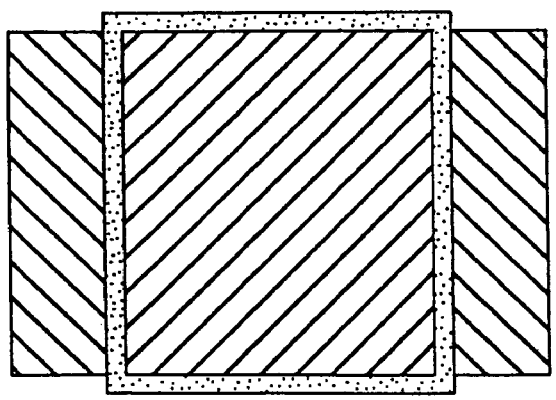
FIG. 6C is a top view of the cage showing the wings expanded.

FIG. 6C is the cage 50 viewed from its top, showing the wings 56 expanded. In a preferred embodiment, the surface of the inner and outer cages has openings to allow bone growth through the cage to achieve bony fusion.

FIG. 7A shows yet another embodiment of the present invention, with a view of the cage 60 end-on. This cage 60 is equipped with two inner cages 66 which slide laterally into the outer cage 68. Affixed to the outer cage 68 are flanges 62 perpendicular to the direction of travel of the inner cages 66. The flanges 62 are provided with screw holes 64 to permit screw insertion into the vertebral body above and below.

FIG. 7B is a side view of the cage 60 in which optional spikes 70 are located on the outside of the outer cage. These spike 70 engage the vertebral bodies to assist in preventing the cage from backing out.

The cages shown in FIGS. 1-7 can be used for Posterior Lumbar Interbody Fusion (PLIF) or Anterior Lumbar Interbody Fusion (ALIF).

In another embodiment of the invention, shown in FIGS. 8A and 8B, which is particularly useful for ALIF, the anterior cage height 81 is greater than the posterior cage height 82 to help maintain lordosis. FIG. 8B is an anterior view of the cage 80 in which the outer cage 83 surrounds the inner cage 84.

For Transforaminal Lumbar interbody fusion, the cage is often banana-shaped. This type of cage is shown in FIGS. 9A and 9B. FIG. 9A is a top view of the cage 90 as inserted, FIG. 9B is a top view of the cage after expansion, showing the outer cage 91 and the inner cage 92.

Another embodiment is shown in FIGS. 10A and 10B. This type of cage 100 is shown in side view in FIG. 10, which shows the two smaller cages 103, 102 partially nesting in the next larger cage. The largest cage 101 contains the middle cage. The anterior of tine assembly is shown at 105, and the posterior is shown at 104.

FIG. 10B shows the cage 100 in position between two vertebrae, 110 and 120. When this cage 100 is placed from a lateral position, the stair-step design of the partially nested cages could mimic a greater height anteriorly as compared to posteriorly, and helps to maintain lordosis.

There are several advantages to the design of the cage according to the present invention:
1. The device is smaller when inserted than conventional cages, thus there is less nerve root retraction required for insertion by a posterior route. This makes injury to the nerve less likely. The small design also lessens the risk of dural tear with subsequent cerebrospinal fluid leakage.
2. The cage can be expanded laterally a variable amount. This provides several advantages:
    a. Lateral expansion allows a larger surface to be exposed to the vertebral body above and below for fusion.
    b. Since the lateral expansion occurs inside the annulus of the disc, there is less likelihood of cage extrusion into the spinal canal.
    c. With expansion, the cage will have a larger volume available for demineralized bone matrix or morselized bone. This allows greater, volume of graft material with increased probability of solid fusion.
3. The cage can be inserted via a posterior lumbar, anterior lumbar, or a transformational approach. The shape of the device can be modified to accommodate the various surgical approaches.

It is to be understood that the phraseology or terminology employed herein is for the purpose of description and not of limitation. The means and materials for carrying out disclosed functions may take a variety of alternative forms without departing from the invention. Thus, the expressions "means to . . . " and "means for . . . " as may be found the specification above, and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above, and it is intended that such expressions be given their broadest interpretation.

What is claimed is:

1. A laterally expandable interbody fusion cage comprising: a. an outer cage having a first inner space defined by the walls of the outer cage; b. at least one inner cage, said at least one inner cage initially being substantially completely inside the first inner space of said outer cage and adapted and constructed to be expanded laterally outwardly from said first inner space in said outer cage; c. each of said at least one inner cage having a second inner space defined by walls of each inner cage said inner space being configured to receive graft material; d. wherein said at least one inner cage and said outer cage have substantially the same configuration; and e. wherein the second inner space in said at least one inner cage is filled with bone graft material prior to expansion, and the first inner space in said outer cage is filled with bone graft material following expansion.

2. The laterally expandable interbody fusion cage according to claim 1 wherein said inner cage is provided with a notch into which an expander fits to move the inner cage laterally.

3. The laterally expandable interbody fusion cage according to claim 1 wherein two inner cages are present wherein a first inner cage and a second inner cage to form two wings, one wing on each side of the outer cage, when the inner cages are expanded laterally from the first space of said outer cage.

4. The laterally expandable interbody fusion cage according to claim 3 wherein the cage has openings sufficient to allow bone growth through the cage.

5. The laterally expandable interbody fusion cage according to claim 1 wherein the anterior height of the cage is greater than the posterior height of the cage.

6. The laterally expandable fusion cage according to claim 1 wherein both the at least one inner cage and the outer cage are shaped like a banana.

7. The laterally expandable interbody fusion cage according to claim 1 wherein both the at least one inner cage and the outer cage have a quadrilateral configuration.

8. The laterally expandable interbody fusion cage according to claim 1 wherein a first inner cage and a second inner cage are nested within the first inner space of the outer cage, and when the first inner cage and the second inner cage are expanded they are expanded on the same side of the outer cage.

9. A laterally expandable interbody fusion cage comprising: a. an outer cage having a first inner space defined by walls of the outer cage and two inner cages which are initially substantially inside the first inner space of the outer cage; b. said inner cages are each adapted and constructed to be expanded laterally outward from the first inner space of said outer cage and each of said inner cages having a second inner space defined by walls of each inner cage; c. said inner cage and said outer cage having substantially the same configuration; d. and two interior flanges provided with screw holes to allow screw insertion into vertebral bodies above and below the cage; and d. wherein the second inner space in each inner cage is filled with bone graft material prior to expansion, and the first inner space in said outer cage is filled with bone graft material following expansion.

10. The laterally expandable interbody cage according to claim 9 wherein outer surfaces of the outer cage are provided with spikes to engage vertebral bodies.

11. The expandable laterally expandable interbody fusion cage according to claim 9 wherein both the inner cages and the outer cage all have a quadrilateral configuration.

12. A method for effecting fusion of two adjacent vertebrae comprising:
    a. exposing an intervertebral disc between the two vertebrae and creating a window in an interior of the disc;
    b. removing nucleus pulposus from the disc;
    c. filling a second inner space in an inner cage defined by walls of the inner cage with fusion material;
    d. inserting a laterally expandable outer cage having a first inner space defined by the walls of the outer cage into the intervertebral space;
    e. moving the inner cage toward the midline of the first inner space of the laterally expandable outer cage; and f. inserting graft material into the first inner space of the outer cage;
g. wherein said inner cage and said outer cage have substantially the same configuration.

13. The method according to claim 12 wherein the laterally expandable interbody fusion cage is inserted anteriorly.

14. The method according to claim 12 wherein the laterally expandable interbody fusion cage is inserted posteriorly.

15. The method according to claim 12 wherein the laterally expandable interbody fusion cage is inserted transforaminally.

16. A laterally expandable interbody fusion cage consisting of: a. an outer cage having a first inner space defined by walls of said outer cage; b. a first inner cage; c. a second inner cage; d. a third inner cage; e. wherein said first and second inner cages are initially nested substantially completely inside the first inner space of the outer cage and are each adapted and constructed to be expanded laterally from said outer cage; f. wherein each of said first, second and third inner cages each have a second inner space defined by walls of each respective inner cage; g. said third inner cage is adapted and constructed to expand laterally from the first inner space of said first inner cage; and h. wherein the second inner space in at least one of said first, second, and third inner cages is filled with bone graft material prior to expansion, and the first inner space in said outer cage is filled with bone graft material following expansion.

17. The linearly expandable laterally expandable interbody fusion cage according to claim 16 wherein the outer cage and the inner cages all have a quadrilateral configuration.

* * * * *